(12) United States Patent
Bachmann et al.

(10) Patent No.: US 6,391,325 B1
(45) Date of Patent: *May 21, 2002

(54) USE OF NITROGEN-CONTAINING COMPLEXING AGENTS FOR DEODORIZATION AND ANTIMICROBIAL TREATMENT OF THE SKIN AND TEXTILE FIBRE MATERIALS

(75) Inventors: Frank Bachmann, Freiburg; Dietmar Ochs, Schopfheim; Roland Utz, Rheinfelden; Thomas Ehlis, Freiburg, all of (DE)

(73) Assignee: Ciba Specialty Chemicals Corporation, Tarrytown, NY (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/180,992
(22) PCT Filed: May 9, 1997
(86) PCT No.: PCT/EP97/02380
§ 371 Date: Nov. 19, 1998
§ 102(e) Date: Nov. 19, 1998
(87) PCT Pub. No.: WO97/44006
PCT Pub. Date: Nov. 27, 1997

(30) Foreign Application Priority Data

May 22, 1996 (DE) ..................... 196 20 644 U

(51) Int. Cl.⁷ .......... A01N 25/00; A61K 9/70; A61K 7/06; A61K 31/195; A61K 31/19
(52) U.S. Cl. .......... 424/405; 424/443; 424/70.1; 424/76.1; 514/561; 514/574
(58) Field of Search ............... 424/405, 443, 424/70.1, 76.1; 514/561, 574

(56) References Cited

U.S. PATENT DOCUMENTS

| | | | |
|---|---|---|---|
| 3,920,020 A | 11/1975 | Kraskin | 128/290 |
| 4,356,190 A | 10/1982 | Kraskin | 424/319 |
| 4,652,585 A | 3/1987 | Gerhardt et al. | 514/563 |
| 5,082,599 A | 1/1992 | Oftring et al. | 252/546 |
| 5,186,856 A | 2/1993 | Holland | 252/143 |
| 5,221,496 A | 6/1993 | Holland | 252/143 |

FOREIGN PATENT DOCUMENTS

| | | |
|---|---|---|
| DE | 1287256 | 1/1969 |
| DE | 1288748 | 2/1969 |
| DE | 3410956 | 9/1985 |
| DE | 3914980 | 12/1990 |
| DE | 4135499 | 5/1992 |
| DE | 4428823 | 2/1996 |
| EP | 0268911 | 6/1988 |
| EP | 0312700 | 4/1989 |
| EP | 0328091 | 8/1989 |
| EP | 0513948 | 11/1992 |
| FR | 7336462 | 5/1974 |
| GB | 1420946 | 1/1976 |
| GB | 2251633 | 7/1992 |
| NL | 7506962 | 12/1975 |
| WO | 94/09105 | 4/1994 |
| WO | 95/12570 | 5/1995 |
| WO | 95/30405 | 11/1995 |
| WO | 96/01803 | 1/1996 |
| WO | 96/04887 | 2/1996 |

OTHER PUBLICATIONS

Abstract for German Pat. No. 1288748, 1969.
Abstract for German Pat. No. 1287256, 1969.
J. Appl. Bact., 1976, 40, pp. 89–99.

(List continued on next page.)

Primary Examiner—Russell Travers
Assistant Examiner—S. Wang
(74) Attorney, Agent, or Firm—Kevin T. Mansfield

(57) ABSTRACT

The present invention relates to the use of nitrogen-containing complexing agents for deodorization and antimicrobial treatment of the skin and of textile fiber materials.

The complexing agents employed according to the invention have the formula

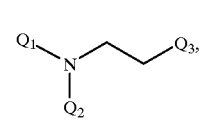

(1)

in which $Q_1$, is $Carb_1$; $Carb_2$; or a radical of the formula $-(CH_2)_{m_1}-OH$;

$Q_2$ is hydrogen or $Carb_2$; and $Q_3$ is $Carb_3$; an amino acid radical; or a radical of the formula

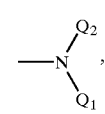

(1a)

where $Carb_1$, $Carb_2$ and $Carb_3$ independently of one another are the radical of a $C_1$–$C_8$-mono- or -dicarboxylic acid and $m_1$ is 1 to 5.

The complexing agents according to the invention show a pronounced bacteriostatic action against *Corynebacterium xerosis* (bacteria which cause body odour) and are therefore suitable as the antimicrobial active substance in body care compositions and antimicrobial fabric finishing of textile materials.

6 Claims, No Drawings

OTHER PUBLICATIONS

Derwent Abstr. 89–193601 for EP 328091, 1989.
Mashihara et al, "Synthesis and Metal chelate stability of N,N'–ethylene–bis(aminomalonic) acid," 1973, Bulletin of the Chemical Society of Japan, vol. 46, p. 844–847.*

Nishikiori et al. "Production by actinomycetes of (S,S)–N, N'–ethylenediaminedisuccinic acid, an inhibitor of phospholipase C," 1984, The Journal of Antibiotics, vol. 17, No. 4, p. 426–427.*

* cited by examiner

USE OF NITROGEN-CONTAINING COMPLEXING AGENTS FOR DEODORIZATION AND ANTIMICROBIAL TREATMENT OF THE SKIN AND TEXTILE FIBRE MATERIALS

The present invention relates to the use of nitrogen-containing complexing agents for deodorization and antimicrobial treatment of the skin and of textile fibre materials.

It is known that various nitrogen-containing complexing agents, for example ethylenediaminetetraacetic acid (EDTA), nitrilotriacetic acid (NTA), β-alaninediacetic acid (EDETA) or ethylenediaminedisuccinic acid (EDDS) are widely employed in domestic detergents because of their complexing properties.

Surprisingly, it has been found that certain nitrogen-containing complexing agents also have an antimicrobial action against Gram-positive bacteria and are therefore particularly suitable for deodorization and antimicrobial treatment of the human skin and of textile fibre materials.

The present invention therefore relates to the use of nitrogen-containing complexing agents for antimicrobial treatment of the skin and of textile fibre materials.

Compounds which are preferably used according to the invention as complexing agents are those of the formula

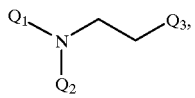

(1)

in which $Q_1$, is $Carb_1$; $Carb_2$,; or a radical of the formula $—(CH_2)_{m_1}—OH$;

$Q_2$ is hydrogen or $Carb_2$; and $Q_3$ is $Carb_3$; an amino acid radical; or a radical of the formula

(1a)

where $Carb_1$, $Carb_2$ and $Carb_3$ independently of one another are the radical of a $C_1$–$C_8$-mono- or dicarboxylic acid; and $m_1$ is 1 to 5.

Compounds which are particularly preferred here are those of the formula (1) in which the amino acid radical $Q_3$ has the formula

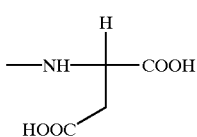

(1b)

and especially compounds of the formula (1) in which $Q_1$ is a monocarboxylic acid; or a radical of the formula $—(CH_2)_{m_1}—OH$;

$Q_2$ is hydrogen or a monocarboxylic acid; and $Q_3$ is formula (1b); or a monocarboxylic acid.

Complexing agents which are of particular interest are those of the formula (1) in which $Carb_2$ and $Carb_3$, independently of one another are the radical of the formula

(1c)

in which $n_1$ is 0 to 5.

Complexing agents which are important in practice have the formula

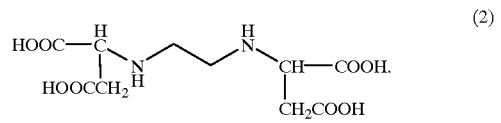

(2)

or the formula

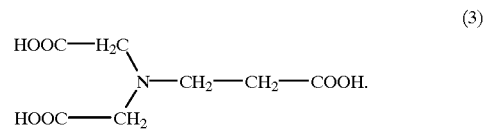

(3)

Nitrilotriacetic acid (NTA) is furthermore suitable as the complexing agent.

Other examples of complexing agents which can be employed according to the invention are aminotrimethylenephosphoric acid (ATMP) of the formula

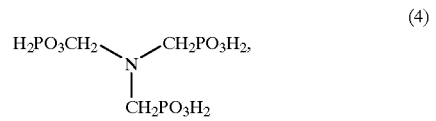

(4)

serinediacetic acid (SDA) of the formula

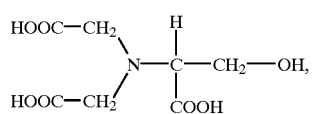

(5)

asparaginediacetic acid of the formula

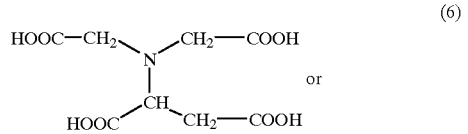

(6)

or methylglycinediacetic acid (MGDA) of the formula (7)

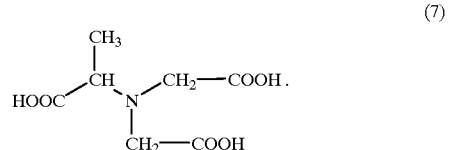

(7)

The nitrogen-containing complexing agents employed according to the invention can be employed not only as the acid but also in the form of the water-soluble salts, preferably as lithium, sodium, potassium, ammonium and ethanolammonium salts.

Ethylenediaminedisuccinic acid (EDDS) of the formula (2) has two asymmetric carbon atoms. Various stereoisomeric forms of this compound are therefore possible. The (S,S) configuration of EDDS has the formula

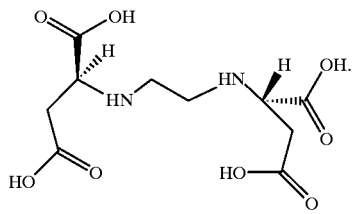

(9)

An inexpensive chemical synthesis leads to a mixture of the three forms S,S; R,R; and meso-EDDS. However, separation of these stereoisomeric compounds requires a high industrial expenditure. Optically pure (S,S)-EDDS can be prepared with the aid of an Actinomycetes strain (T. Nishikiori et al., Production by Actinomycetes of (S,S)-N,N'-ethylenediaminedisuccinic acid, an inhibitor of phospholipase c; J.Antibiotics 37, 426–427 (1984)).

The purely chemical preparation of the compound of the formula (9) is carried out in a manner known per se, such as is described, for example, by J. A. Neal, N. Rose in Inorganic Chemistry,7, 2405 (1985).

Racemic EDDS can be prepared in accordance with U.S. Pat. No. 3,158,635.

The complexing agents according to the invention show a pronounced bacteriostatic action, in particular against Gram-positive bacteria of the skin flora, for example *Corynebacterium xerosis* (bacteria which causes body odour). They are therefore particularly suitable as the antimicrobial active substance in body care compositions, for example soaps, shampoos, foot care products and, in particular, deodorants, as well as an additive in detergents.

The invention therefore also relates to a body care composition comprising at least one nitrogen-containing complexing agent and carriers or auxiliaries which are tolerated in comsetics.

The body care composition according to the invention comprises 0.01 to 15, preferably 0.5 to 10, % by weight, based on the total weight of the composition, of a nitrogen-containing complexing agent and auxiliaries which are tolerated in cosmetics.

Depending on the form in which the body care composition is present, it also comprises, in addition to the complexing agent, other constituents, for example sequestering agents, dyes, perfume oils, thickeners or consolidating agents (consistency regulators), emmollients, UV absorbers, skin protection agents, antioxidants, additives which improve the mechanical properties, such as dicarboxylic acids and/or Al, Zn, Ca, or Mg salts of $C_{14}$–$C_{22}$ fatty acids, and, if appropriate, preservatives.

Because of their good water-solubility, the complexing agents according to the invention can be incorporated into the corresponding formulations without problems.

The body care compositions according to the invention can be formulated as a water-in-oil or oil-in-water emulsion, as alcoholic or alcohol containing formulation, as a vesicular dispersion of an ionic or nonionic amphiphilic lipid, as a gel or solid stick or as an aerosol formulation.

As a water-in-oil or oil-in-water emulsion, the auxiliary which is tolerated in cosmetics preferably comprises 5 to 50% of an oily phase, 5 to 20% of an emulsifier and 30 to 90% of water. The oily phase can comprise any oil suitable for cosmetic formulations, for example one or more hydrocarbon oils, a wax, a naturally occurring oil, a silicone oil, a fatty acid ester or a fatty alcohol. Preferred mono- or polyols are ethanol, isopropanol, propylene glycol, hexylene glycol, glycerol and sorbitol.

An anitmicrobial soap has, for example, the following composition:

0.01 to 5% by weight of the compound of the formula (2)

0.3 to 1% by weight of titanium dioxide 1 to 10% by weight of stearic acid to 100% of soap base, for example the sodium slats of tallow fatty and coconut fatty acid or glycerols.

A shampoo has, for example, the following composition:

0.01 to 5% by weight of the compound of the formula (2), 12.0% by weight of sodium laureth-2-sulfate, 4.0% by weight of cocamidopropylbetaine, 3.0% by weight of NaCl and water to 100%.

A deodorant has, for example, the following composition:

0.01 to 5% by weight of the compound of the formula (2),

60% by weight of ethanol, 0.3% by weight of perfume oil and water to 100%.

The complexing agents according to the invention are furthermore suitable for the treatment of textile fibre materials. The fibre materials are non-dyed and dyed or printed fibre materials, for example of silk, leather, wool, polyamide or polyurethanes, and in particular all types of cellulosic fibre materials. Such fibre materials are, for example, naturally occurring cellulosic fibres, such as cotton, linen, jute and hemp, and cellulose and regenerated cellulose. Textile fibre materials which are preferably suitable are those of cotton.

The following examples serve to illustrate the invention.

EXAMPLE 1

Determination of the Antimicrobial Activities of S, S-EDDS, R,R-EDDS, Racemate of EDDS and EDETA, EDTA and NTA Test method: An agar diffusion test is carried out with the following modifications:

Medium: casein-soya flour peptone agar (caso-agar)

Test organisms: *Corynebacterium xerosis* ATCC 373 *Corynebacterium xerosis* ATCC 7711 *Corynebacterium minutissimum* ATCC 23358

Procedure: 500 ml of caso-agar are innoculated with 3.5 ml of an overnight culture of the bacteria, diluted 1:100, and caso plates (18 ml) are covered with a layer of about 5 ml of the bacteria-containing agar. After the plates have cooled, holes of diameter 1 cm are stamped out with a cork borer. Each stamped-out hole is filled with in each case 100 μl of a test substance dilution and the plates are incubated at 37° C. for 2 days. Double-distilled water is employed as the solvent for all the substances. In the case of EDETA GS, the pH is adjusted to 3.3 by addition of 1 N NaOH. Chemically prepared S,S-EDDS is adjusted to the pH of 5.6 by addition of 1 N NaOH.

Controls: Double-distilled water

The test results are listed in Table 1:

TABLE 1

| Substance | Concentration [ppm] | Inhibitory aureola diameter | |
|---|---|---|---|
| | | Cory. xerosis ATTC 7711 | Cory. xerosis ATTC 373 |
| EDETA | 10000 | 5/5[1] | 1/1[1] |
| S,S-EDDS (prepared chemically) | 10000 | 15/15[1] | 10/10[1] |
| S,S-EDDS (prepared by fermentation) | 10000 | 15/15[1] | 10/10[1] |
| EDTA | 10000 | 2/2 | 5/5 |
| R,S-EDDS | 10000 | n.d. | 12/13 |
| R,R-EDDS | 10000 | n.d. | 15/15 |

[1]Slight growth on inhibitory aureolas

The test results show that both EDETA, EDTA and the EDDS prepared by fermentation and chemically (=R,R; S,S; R,S) show a pronounced bacteriostatic action against *Corynebacterium xerosis*.

Examples of Formulations Having a Bacteriostatic Action

EXAMPLE 2

Preparation of a Washing Powder

| Laurylammonium sulfate | 8.0% |
|---|---|
| Nonionic surfactants | 2.9% |
| Soaps | 3.5% |
| Sodium tripolyphosphate | 43.8% |
| Sodium silicate | 7.5% |
| Magnesium silicate | 1.9% |
| Carboxymethylcellulose | 1.2% |
| EDTA | 0.2% |
| Sodium sulfate | 21.2% |
| EDDS | 1% |
| Water | to 100% |

The formulation is prepared as follows:

The solid components are mixed and homogenized in a mortar and stirred with deionized water until a uniform pourable and pumpable paste (slurry) is obtained, which is finally spray-dried.

EXAMPLE 3

Preparation of a Cleansing Tonic

| Ethanol | 20% |
|---|---|
| Glycerol | 5% |
| PEG-40 hydrogenated castor oil (hydrogenated ethoxylated castor oil) | 1% |
| EDDS | 0.5% |
| Perfume | ad libidum |
| Water | to 100% |

The formulation is prepared as follows:

EDDS is dissolved in ethanol. Under stirring at room temperature PEG-40, glycerol and perfume are added. Finally, the water is added.

EXAMPLE 3

Preparation of a Deodorant Stick

| Ethanol | 20% |
|---|---|
| Glycerol | 30% |
| Propylene glycol | 20% |
| Ceteareth-25 (= ethoxylated cetyl/stearyl alcohol) | 3% |
| Sodium stearate | 7% |
| EDDS | 0, 5% |
| Perfume | ad libidum |
| Water | to 100% |

The formulation is prepared as follows:

Sodium stearate is melted at 60° C. Propylene glycol, Cetearath-25 and glycerol are added to the melting until a homogeneous clear suspension is obtained. Finally, the suspension is stirred with a EDDS-solution in an alcohol/water mixture at 50° C. and cooled slowly.

EXAMPLE 4

Preparation of Soluble EDDS Salts and Deodorant Formulations

S,S-EDDS is obtained by means of microbiological (WO 96/36725) or chemical synthesis (J. A. Neal et al., Inorg.Chem. 7, 2405 (1968)). Racemic EDDS is prepared from maleic anhydride and ethylenediamine (U.S. Pat. No. 3,158,635).

A 1% suspension of racemic EDDS or S,S-EDDS is prepared in water/ethanol (about 7:3) with vigorous stirring. An aqueous solution of NaOH is metered in with an autoamtic titration device until the pH of 7 remains constant for 30 minutes. Any slight milky clouding which occurs is removed by filtering through paper.

By addition of a thickener like hydroxy ethyl cellulose a clear deodorant formulation which is stable at room temperature, comprises about 1% of active substance (based on the tetra-acid) and has a skin-friendly pH is obtained.

If NaOH is replaced by KOH, ammonia or ethanolamine, the corresponding potassium, ammonium and ethanolammonium salts are obtained. Lithium hydroxide, sodium carbonate, sodium bicarbonate or laurylamine can also be employed as the base.

EXAMPLE 5

Detection of the Substantial Antimicrobial Activity of R,S-EDDS Salts on the Skin

| Formulations (Solutions in 30% ethanol): | 1% of R,S-EDDS/sodium salt |
|---|---|
| | 1% of R,S-EDDS/amine salt |
| | (for the preparation, cf. Example 4) |
| Medium: | Casein-soya flour peptone agar (caso-agar) |
| Test organism: | Corynebacterium xerosis ATCC 373 |

Test method:

Before application of the test solutions, the underarms are washed with a non-antimicrobial soap twice for 1 minute each time. A total of 6 ml of test product is then applied to the washed, dry skin of the underarm. Immediately and 2 hours after application of the test products, the EDDS on the skin is extracted by means of discs of filter paper (2 cm diameter) moistened in 0.9% NaCl solution (pH: 8.2). For this, the moist filter disc is placed on the treated skin without airbubbles for 4 minutes. The filter discs are subsequently dried at room temperature and then placed on solid agar media with test bacteria.

To prepare the solid agar media, 500 ml of liquid agar are innoculated with 3.5 ml of a 12–16-hour culture, diluted 1:100, of the test bacteria at 47° C. and caso plates (18 ml) are covered with a layer of about 5 ml of the bacteria-containing agar.

After the filter discs have been placed on top, the agar media are incubated for 2 days at 37° C. and the inhibition under the filter disc or the inhibitory aureolas of the filter discs is/are then determined.

The test results are listed in Table 2:

TABLE 2

| Substance | | Inhibitory aureola diameter (mm)/inhibition under the filter disc* Coryneb. xerosis ATCC 373 |
|---|---|---|
| Placebo | | 0/0 |
| R,S-EDDS (sodium salt) | | |
| | immediately | 5/4 |
| | 2 hours after application | 3/4 |
| R,S-EDDS (Amine salt) | | |
| | immediately | 2, 5/4 |
| | 2 hours after application | 2/4 |

*Inhibition under the filter disc:
Explanation:
0 = good growth (no inhibition)
2 = inhibited but clear growth (weak inhibition)
4 = no growth (potent inhibition)

The test results show that a pronounced inhibition of *Corynebacterium xerosis* is achieved with both test substances.

The test shows that sufficiently high concentrations of EDDS to achieve inhibition of *Corynebacterium xerosis* are also still present on the skin 2 hours after the last application.

What is claimed is:

1. A method of antimicrobial treatment of the skin or of textile fibre materials which comprises contacting them with an antimicrobially effective amount of a nitrogen-containing complexing agent of the formula

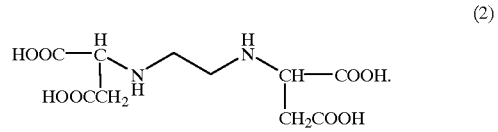

(2)

2. A method according to claim 1 wherein the nitrogen-containing complexing agent of the formula (2) is in the form of its (S,S), (R,S) or (R,R) stereoisomer.

3. A method according to claim 1, wherein the complexing agent is in the form of one of its water-soluble salts.

4. A method according to claim 3, wherein the complexing agent is present in the form of its lithium, sodium, potassium, ammonium or ethanolammonium salt.

5. A method of combating Gram-positive bacteria which comprises contacting them with an antimicrobially effective amount of a nitrogen-containing complexing agent according to claim 1.

6. A method disinfecting textile fibre materials, which comprises contacting said materials with an antimicrobially effective amount of a nitrogen-containing complexing agent according to claim 1.

* * * * *

UNITED STATES PATENT AND TRADEMARK OFFICE
CERTIFICATE OF CORRECTION

PATENT NO.     : 6,391,325 B1
DATED          : May 21, 2002
INVENTOR(S)    : Frank Bachmann et al.

It is certified that error appears in the above-identified patent and that said Letters Patent is hereby corrected as shown below:

<u>Title page,</u>
Item [30], should read:
-- May 22, 1996 (DE)..............................196 20 644.8 --.

Signed and Sealed this

Twenty-second Day of October, 2002

Attest:

Attesting Officer

JAMES E. ROGAN
Director of the United States Patent and Trademark Office